US008167879B2

(12) United States Patent
Haufe

(10) Patent No.: US 8,167,879 B2
(45) Date of Patent: May 1, 2012

(54) COMBINATION TISSUE REMOVAL AND CAUTERIZATION INSTRUMENT

(75) Inventor: Scott M. W. Haufe, Niceville, FL (US)

(73) Assignee: Scott M. W. Haufe, Destin, FL (US)

( * ) Notice: Subject to any disclaimer, the term of this patent is extended or adjusted under 35 U.S.C. 154(b) by 586 days.

(21) Appl. No.: 12/361,184

(22) Filed: Jan. 28, 2009

(65) Prior Publication Data
US 2010/0191234 A1 Jul. 29, 2010

(51) Int. Cl.
A61B 18/18 (2006.01)
(52) U.S. Cl. .......................................... 606/49
(58) Field of Classification Search .................. 604/22; 606/32–41
See application file for complete search history.

(56) References Cited

U.S. PATENT DOCUMENTS

| 2,012,363 | A | * | 8/1935 | Vogel ............................. 604/22 |
| 4,991,578 | A | | 2/1991 | Cohen |
| 5,807,395 | A | | 9/1998 | Mulier et al. |
| 5,855,576 | A | | 1/1999 | LeVeen et al. |
| 5,957,863 | A | | 9/1999 | Koblish et al. |
| 6,416,490 | B1 | * | 7/2002 | Ellis et al. ...................... 604/22 |
| 6,770,070 | B1 | | 8/2004 | Balbierz |
| 7,361,174 | B2 | | 4/2008 | Bee et al. |
| 2005/0245923 | A1 | | 11/2005 | Christopherson et al. |
| 2006/0058780 | A1 | | 3/2006 | Edwards et al. |
| 2006/0095059 | A1 | | 5/2006 | Bleich et al. |
| 2007/0049920 | A1 | | 3/2007 | McClurken et al. |
| 2007/0129719 | A1 | | 6/2007 | Kendale et al. |
| 2007/0293724 | A1 | | 12/2007 | Saadat et al. |
| 2008/0015565 | A1 | | 1/2008 | Davison |
| 2008/0161670 | A1 | | 7/2008 | King et al. |

OTHER PUBLICATIONS

Product literature for "Shaver Systems", downloaded from <http://global.smith-nephew.com/us/Endoscopy_catalogues.htm> on Dec. 31, 2008.

* cited by examiner

Primary Examiner — Manuel Mendez
(74) Attorney, Agent, or Firm — Banner & Witcoff, Ltd.

(57) ABSTRACT

A combination tissue removal and cauterization instrument includes one or more heads configured to remove tissue by mechanical cutting action resulting from rotation, vibration and/or other type of powered motion. The heads also have electroconductive outer surfaces to which electrical energy is supplied, thereby permitting the heads to simultaneously cauterize tissue that is not removed.

15 Claims, 18 Drawing Sheets

COMBINATION TISSUE REMOVAL AND CAUTERIZATION INSTRUMENT

BACKGROUND

It is often appropriate in many surgical procedures to selectively remove small portions of body tissue. This is indicated, for example, with regard to tissue that may be diseased or damaged. It may be necessary to remove diseased or damaged tissue so that remaining tissue can heal and/or to prevent spread of a disease to healthy tissue. As another example, it is sometimes beneficial to remove tissue that is being compressed or otherwise impinged upon by other body structures. By removing the impinged tissue, it is often possible to alleviate patient discomfort. One specific example of such a procedure is a facet debridement performed on a cervical, thoracic or lumbar facet joint of a human spine. During a facet debridement, the synovial capsule between facets is removed so as to denude the bone and deinervate the joint.

Various types of instruments are available to remove tissue as part of a surgical procedure. Some types of tissue can be effectively removed using electro-ablative techniques. In particular, electrical energy heats an instrument cutting tip that is used to burn away unwanted tissue. Some types of tissue, however, are more effectively removed by mechanical cutting action of a blade, grinder or other type of instrument.

When removing tissue, it is often necessary to cauterize remaining tissue. This cauterization may be needed to stop bleeding, to prevent regrowth of removed tissue, and/or for other purposes. When using electro-ablative techniques, cauterization and tissue removal can often be performed simultaneously. With mechanical cutting instruments, however, a separate cauterization instrument is needed. This often means that a surgeon must revisualize the operative site after changing instruments and locate the area to be cauterized. This can be especially problematic in laparoscopic procedures. Specifically, the surgeon must remove the grinder or other mechanical cutting instrument from a cannula, inserts a cauterization instrument, and then cauterize the appropriate region.

SUMMARY

This Summary is provided to introduce a selection of concepts in a simplified form that are further described below in the Detailed Description. This Summary is not intended to identify key features or essential features of the invention.

In an instrument according to at least some embodiments, one or more heads is configured to remove tissue by mechanical cutting action resulting from rotation, vibration and/or other type of powered motion of the head(s). The heads also have electroconductive outer surfaces to which electrical energy is supplied, thereby permitting the heads to simultaneously cauterize tissue that is not removed. The instrument is sized and configured for insertion into a surgical cannula so as to reach target tissue during a laparoscopic surgical procedure.

BRIEF DESCRIPTION OF THE DRAWINGS

Some embodiments of the present invention are illustrated by way of example, and not by way of limitation, in the figures of the accompanying drawings and in which like reference numerals refer to similar elements.

DETAILED DESCRIPTION

Figure 1:
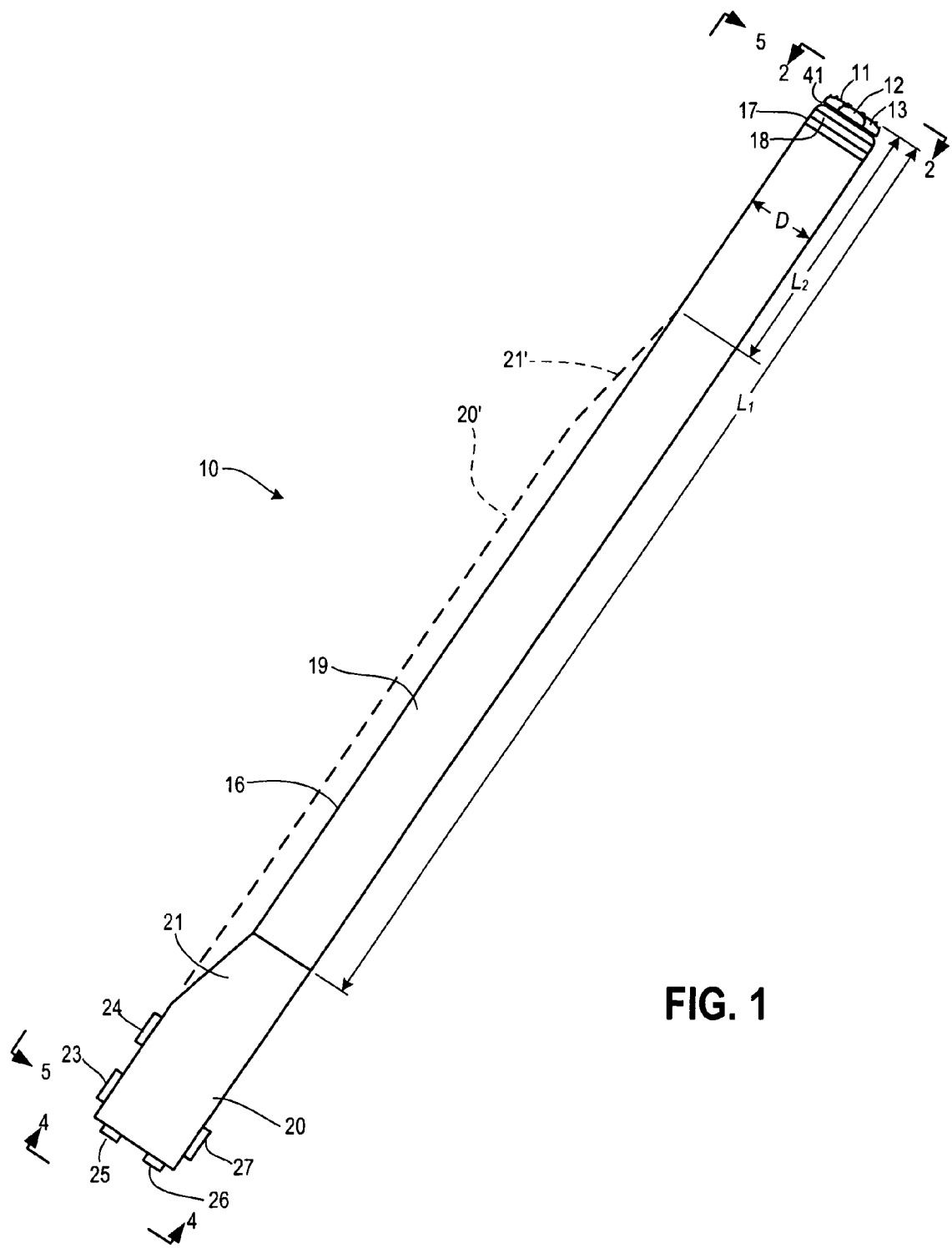
FIG. 1 is a side view of a combination tissue removal and electrical cauterization surgical instrument according to some embodiments.

FIG. 1 is a side view of a combination tissue removal and electrical cauterization surgical instrument 10 according to some embodiments. Four rotating metal heads 11, 12, 13 and 14 are located on a distal outer face 41 of instrument 10. Only heads 11-13 are visible in FIG. 1. All four heads 11-14 can be seen in FIG. 2, an enlarged end view of instrument 10 from the location shown in FIG. 1. Each of heads 11-14 rotates relative to the distal outer face 41 of instrument 10 and includes a plurality of teeth 15 distributed on the head outer surface. When heads 11-14 rotate and are urged into contact with tissue in a patient's body, the mechanical cutting action of teeth 15 removes portions of that tissue. The exposed metal outer surfaces of heads 11-14 are used to conduct electrical energy to remaining tissue in the same region. In this manner, a surgeon can use instrument 10 to remove unwanted tissue from a surgical region while simultaneously cauterizing other tissue that is exposed by removal of the unwanted tissue. As but one example, instrument 10 can be used during a spinal facet joint debridement procedure to remove synovial tissue from a facet joint and simultaneously cauterize a bone surface of the facet joint that is exposed by removal of the synovial tissue. As another example, instrument 10 and/or instruments according to other embodiments can be used to denude and deinervate various other joints (e.g., the sacroiliac joint).

The outer body of instrument 10 includes a main body portion 16 formed from a nonconductive polymer material. An end cap 17 is attached to main body 16 at the distal end and holds heads 11-14. A conductive ring 18 is also located in end cap 17, and is discussed below. Main body 16 includes an elongated neck 19 that extends along a substantial portion of the total length of instrument 10, a handle region 20, and a transition region 21 joining handle 20 and neck 19. In at least some embodiments, neck 19, end cap 17 and heads 11-14 are sized for insertion into a cannula or sheath used during a laparoscopic surgical procedure. The combined length $L_1$ of neck 19, end cap 17 and heads 11-14 along a longitudinal axis of instrument 10 will vary in different embodiments. Similarly, the outer diameter D of neck 19, end cap 17 and heads 11-14 will also vary depending on the particular embodiment being considered. In at least some embodiments, length $L_1$ is between 100 millimeters (mm) and 150 mm and diameter D is between 5 mm and 15 mm. In some embodiments, and as shown in FIG. 1 with a broken line, a handle 20' and a transition region 21' occupy a larger percentage of the total instrument length, with the portion sized for insertion into a cannula or sheath having a length $L_2$ between 6 and 20 mm. Neck 19 and end cap 17 are generally cylindrical in shape, although this need not of be the case. In other embodiments, elongate neck 19 and/or end cap 17 may have an oval, polygonal or other non-circular cross-section. In some such embodiments, the distal end also has a maximum dimension D perpendicular to a longitudinal axis of 5 to 15 mm.

Figure 2:
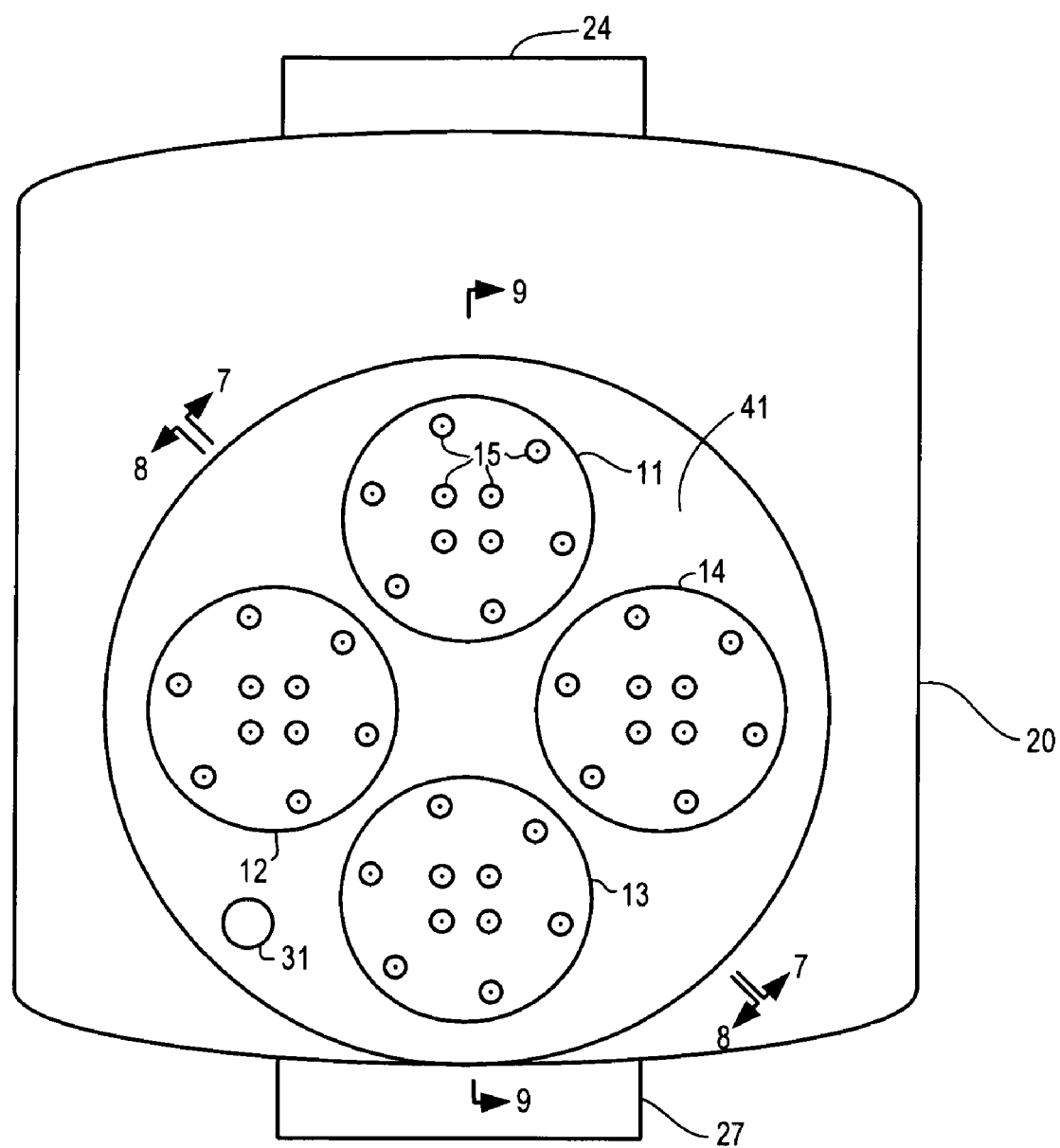
FIG. 2 is an enlarged distal end view of the instrument of FIG. 1.
Figure 3:
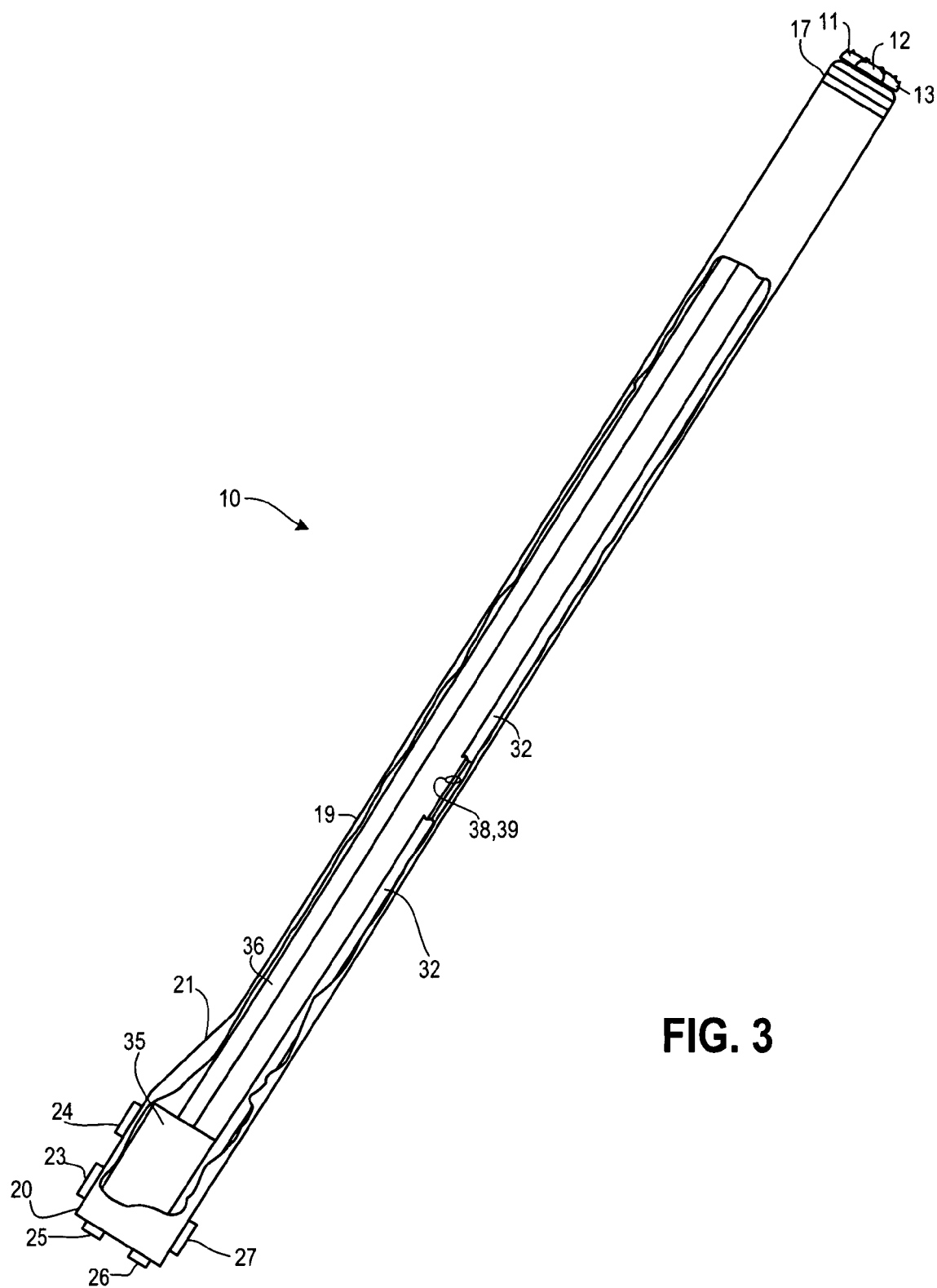
FIG. 3 is a side view of the instrument of FIG. 1, but with a portion of the main body removed so as to show internal components.

Handle region 20 houses a drive motor 35 used to supply rotational torque for turning heads 11-14. Drive motor 35 is not visible in FIG. 1, but can be seen in the partial cutaway view of FIG. 3. FIG. 3 is a side view of instrument 10 similar to FIG. 1, but with a portion of main body 16 removed so as to show internal components of instrument 10. A drive shaft 36 couples motor 35 to head 11. As described in more detail below, head 11 is coupled to heads 12, 13 and 14 such that rotation of head 11 also causes rotation of heads 12, 13 and 14. Also seen within the cut-away portion of FIG. 5 is power supply wire 38 used to transfer electrical cauterization energy to the surfaces of heads 11-14 and wire 39 used for return current when electrocauterizing in bipolar mode. A guide wire tube 32 connects hole 33 (seen in FIG. 4) with hole 31 in distal outer face 41 (FIG. 2), as is discussed below. So as to show wires 38 and 39, which lie behind tube 32 in the view of FIG. 3, a portion of tube 32 is removed in FIG. 3. Although not shown in FIG. 3, handle 20 also contains control electronics for drive motor 35.

A first connector 23 on handle 20 is configured for attachment to a commercially-available electrosurgical generator that provides electrical cauterizing energy. Connector 23 is attached to wires 38 and 39 and configured to place wires 38 and 39 into electrical communication with corresponding conductors in a generator cable. Because the power requirements for drive motor 35 will typically differ from the power used for electrical cauterization, a second connector 24 is configured for attachment to a separate power source for drive motor 35. In certain embodiments, handle 20 contains a battery power source for the drive motor. In still other embodiments, handle 20 includes power conversion electronics that tap a portion of the electrical energy received at first connector 23 and converts that energy for use in powering the drive motor. Located on a proximal face of handle 20 are control switches 25 and 26. Switch 25 is used to activate and deactivate motor 35 so as to start and stop rotation of heads 11-14. Switch 26 is used to activate and deactivate the flow of electrical cauterizing energy to the outer surfaces of heads 11-14. In some embodiments, additional controls (e.g., a head rotation speed adjustment knob) are also located on the proximal face or elsewhere on handle 20. In still other embodiments, a control cable connector 27 is configured to receive a control cable that places instrument 10 in communication with one or more remotely located switches (e.g., foot switches) that control rotation of heads 11-14 and/or the supply of cauterizing electrical energy to the surfaces of heads 11-14. In yet other embodiments, instrument 10 includes a single connector configured for attachment to a cable having conductors supplying electrical energy to power drive motor 35, conductors providing electrical cauterization energy, and/or control wires carrying signals to activate and deactivate drive motor 35.

Figure 4:
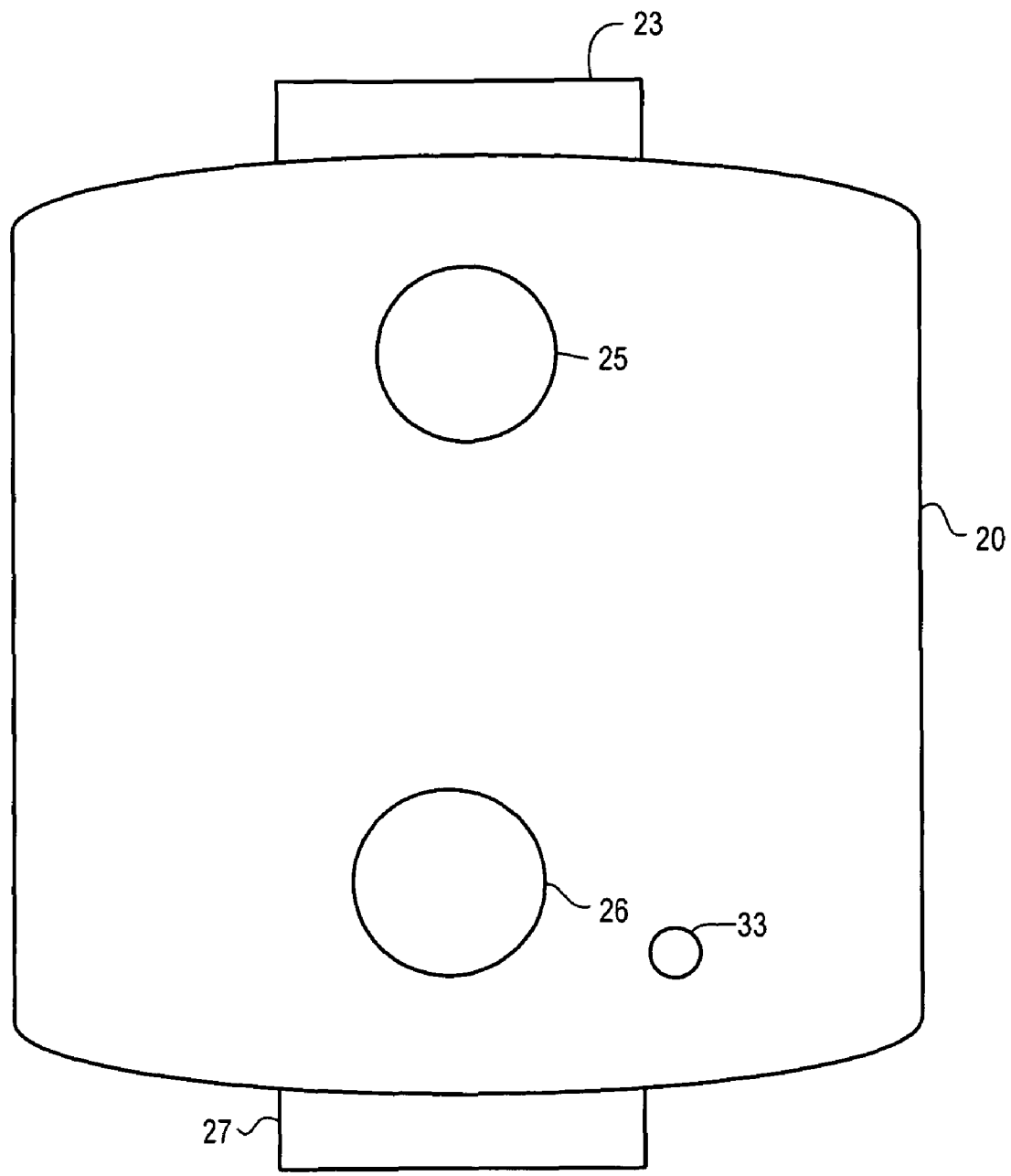
FIG. 4 is an enlarged proximal end view of the instrument of FIG. 1.
Figure 5:
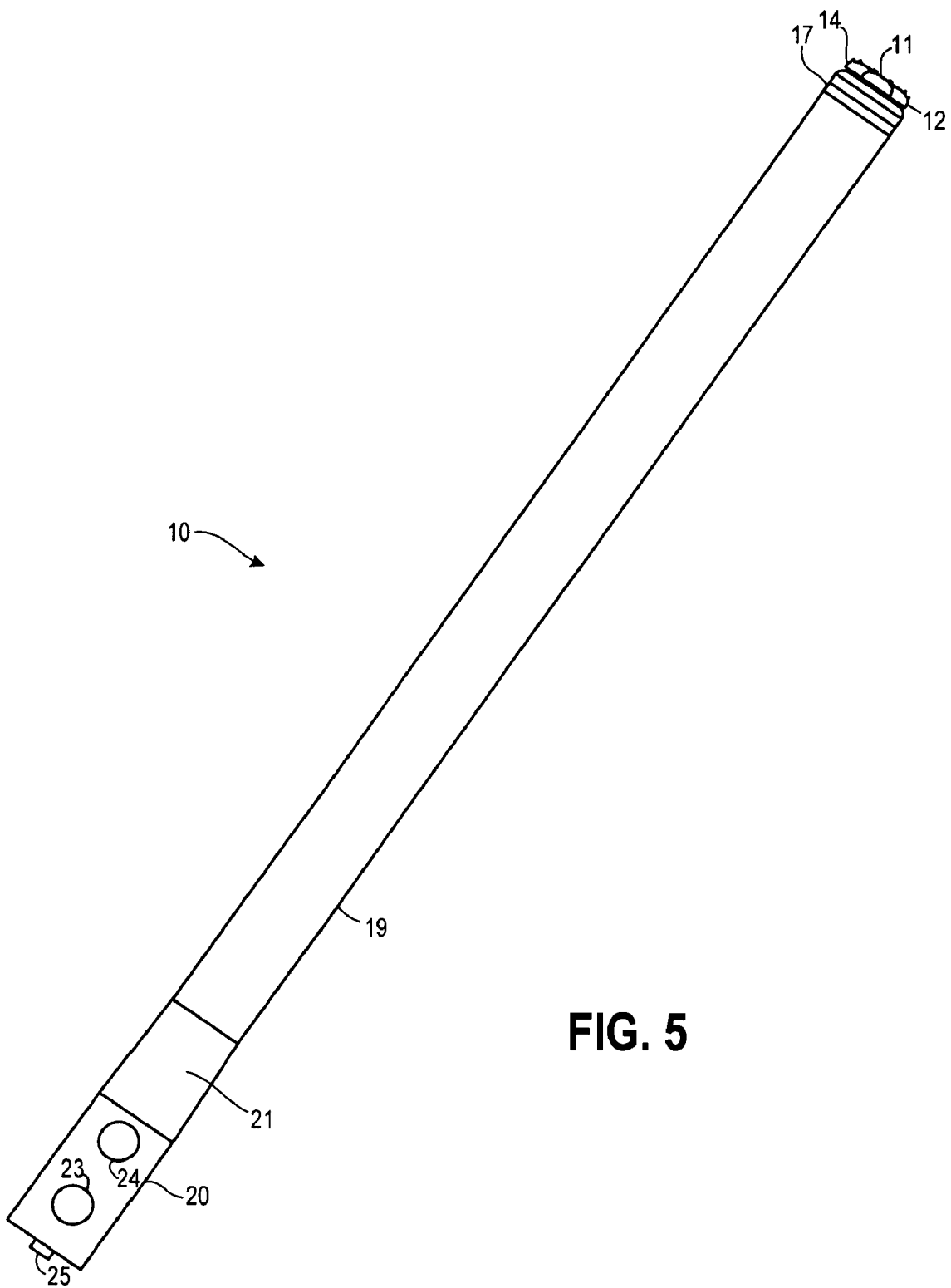
FIG. 5 is a top view of the instrument of FIG. 1.

FIG. 4 is an enlarged proximal end view of instrument 10 taken from the location shown in FIG. 1, and shows controls 25 and 26 and exit hole 33 of guide wire tube 32. FIG. 5 is a top view of instrument 10 taken from the location shown in FIG. 1. The outer dimensions of handle 20 are somewhat larger than the outer diameter D of neck 19. As seen in FIG. 3, this enlargement provides additional internal space to accommodate drive motor 35. The greater surface area of handle 20 also provides a portion of instrument 10 that a physician can more easily grasp and manipulate while wearing surgical gloves. In some embodiments, additional surface features can be included on handle 20. As but one example, a series of small bumps and/or ridges can be distributed along the outer surface of handle 20 and/or along the surface of transition region 21. Handle 20 could be extended so as to provide a longer gripping portion. Handle 20 could also include curved surface contours generally corresponding to locations of a physician's fingers.

Figure 6:
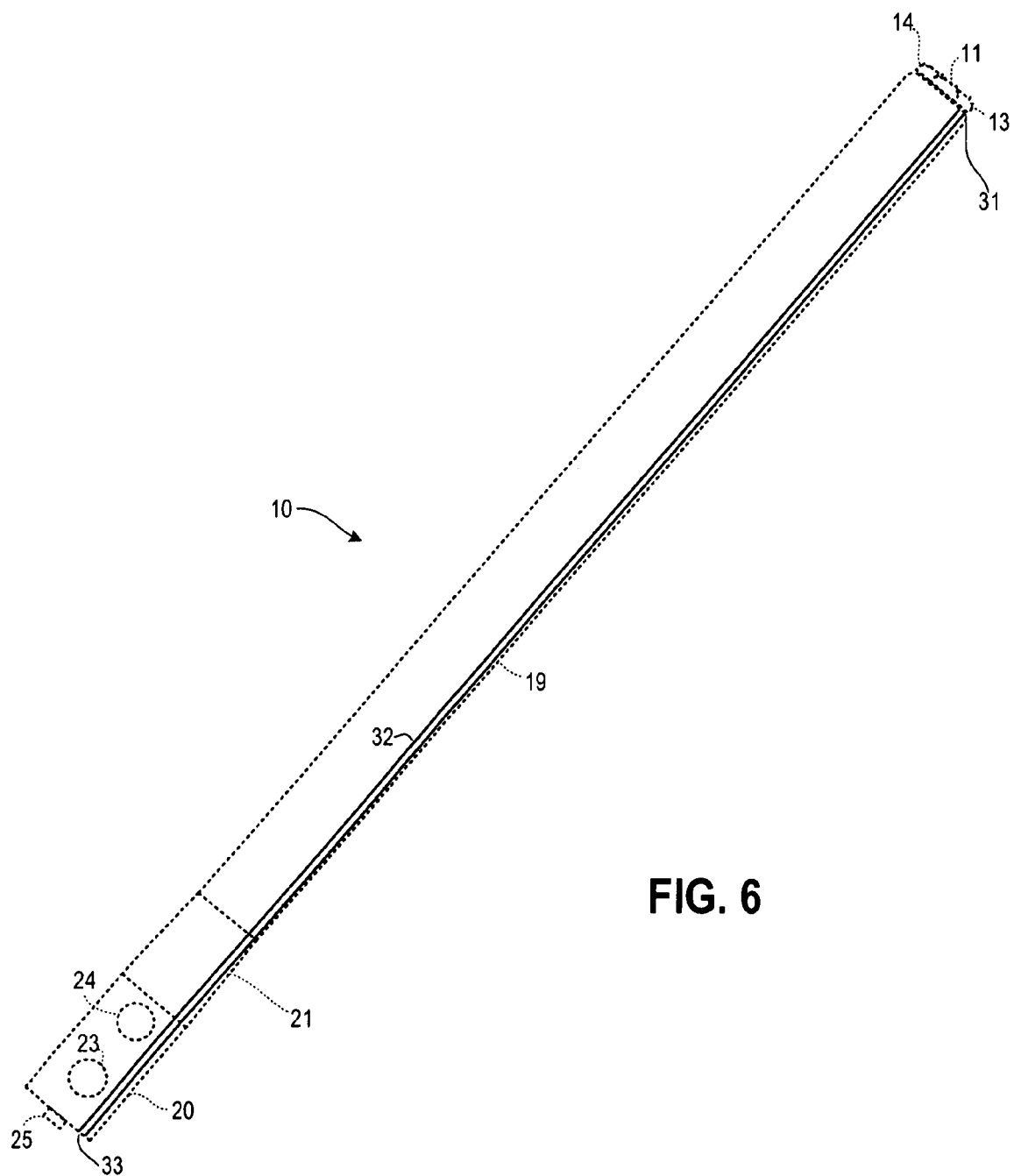
FIG. 6 another top view of the instrument of FIG. 1, but with the outline of the main body, end cap and heads shown in broken lines.

Many surgical procedures employ a guide wire to place instruments into a desired location inside of a patient's body. After placing a first end of a guide wire in the desired location, instruments can be threaded over a second end of the guide wire (typically outside of the patient) and slid over that wire to the surgical site. In at least some embodiments, and as seen in FIGS. 1, 2 and 6, instrument 10 is configured for use with a guide wire. Specifically, a guide wire entrance hole 31 located in distal outer face 41 of instrument 10 (see FIG. 2) is connected by an internal conduit to a guide wire exit hole 33 located on the side of instrument 10 (see FIG. 1). As seen in FIG. 6, a top view of instrument 10 with the outline of main body 16, end cap 17 and heads 11-14 shown in broken lines, the internal conduit can take the form of a tube 32 attached with sealed connections to holes 31 and 33. In some embodiments, guide tube 32 is also sized so as to facilitate introduction of fluids to the operative region and/or to withdraw fluids from the operative region.

Figure 7:
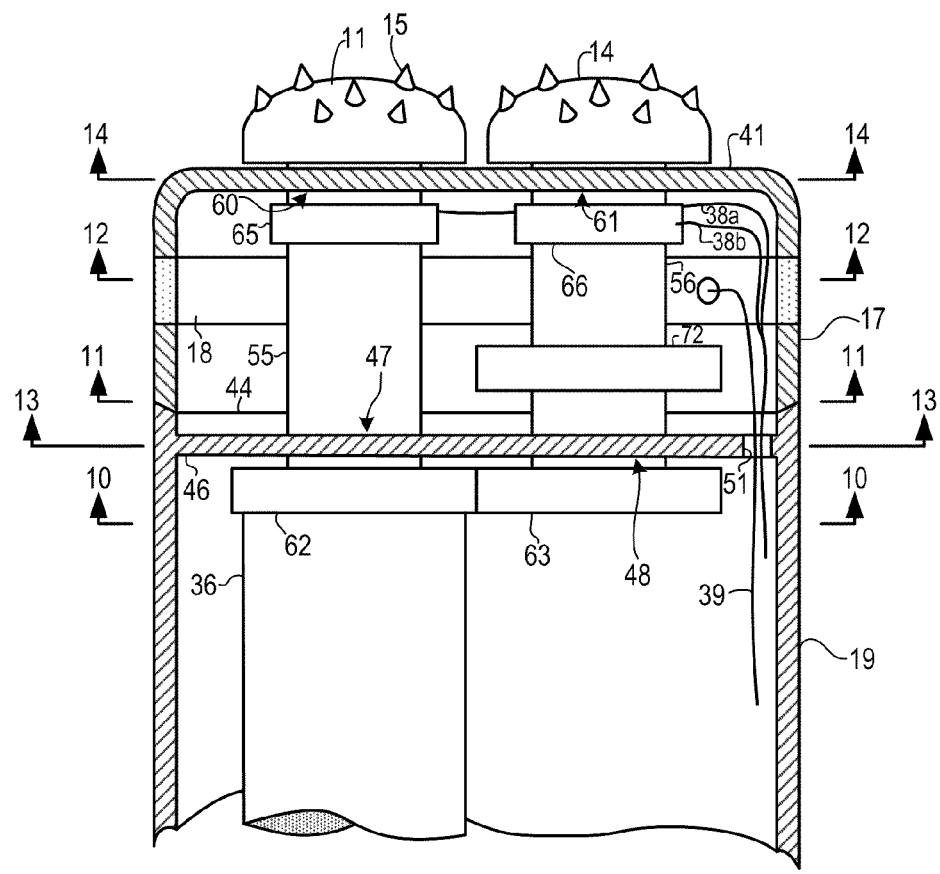
FIGS. 7 and 8 are longitudinal cross-sectional views, taken from the planes indicated in FIG. 2, showing opposite sides a distal end portion of the instrument of FIG. 1.
Figure 8:
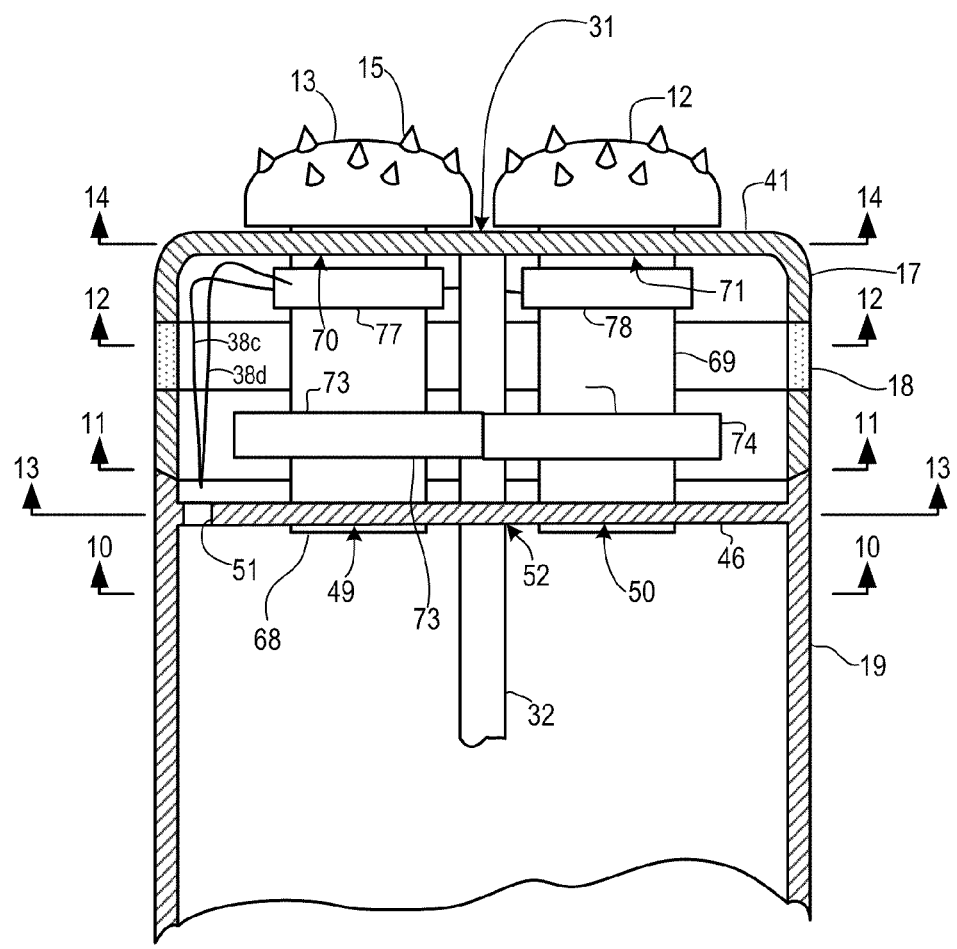
Figure 9:
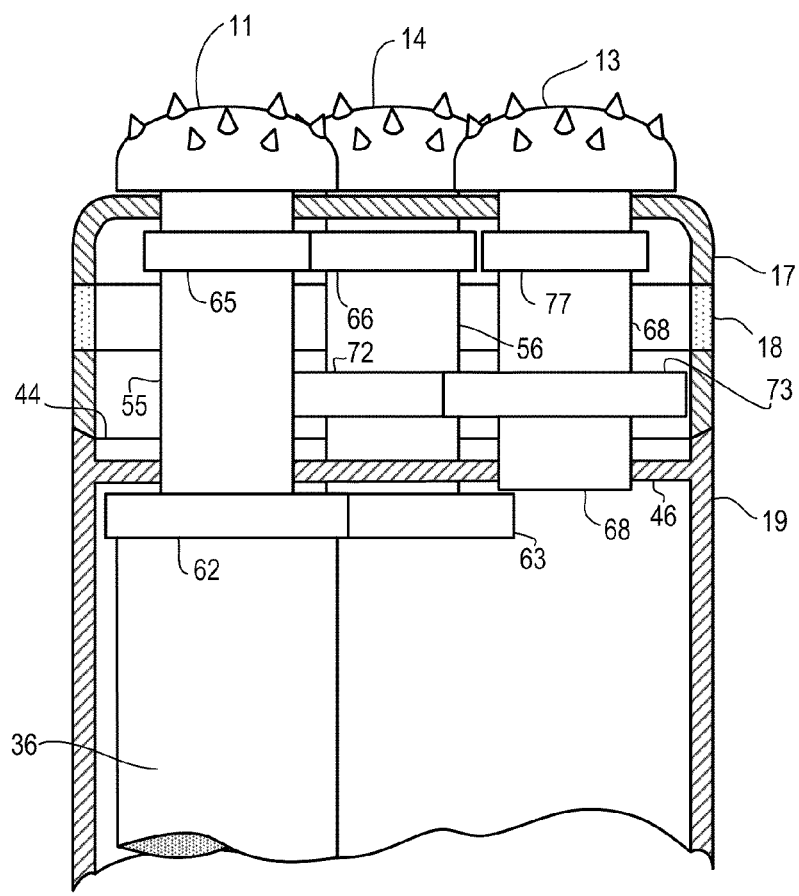
FIG. 9 is another longitudinal cross-sectional view of the instrument of FIG. 1, but taken from a different plane indicated in FIG. 2.

FIG. 7 is a longitudinal cross-sectional view, taken from the plane indicated in FIG. 2, of a portion of instrument 10 near the distal end. FIG. 8 is also cross-sectional view of a portion of instrument 10 near the distal end, and taken from the plane indicated in FIG. 2. As can be appreciated from FIG. 2, FIGS. 7 and 8 show thus show opposite halves of the distal end. FIG. 9 is an alternate cross-sectional view, taken from another plane shown in FIG. 2, showing several of the components seen in FIGS. 7 and 8. Throughout the drawings, cross-hatching and stippling are used to indicate the presence of separate physical elements, but should not be construed as requiring a particular type of material.

Figure 13:
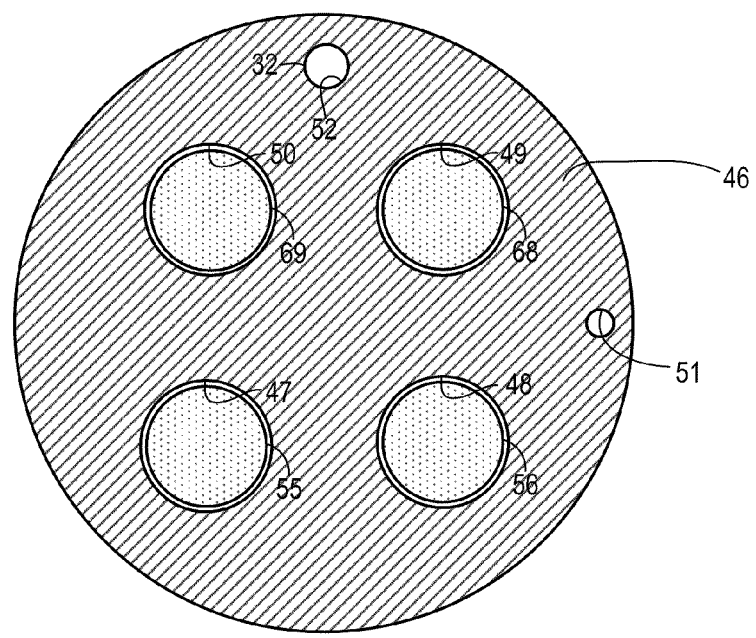
Figure 14:
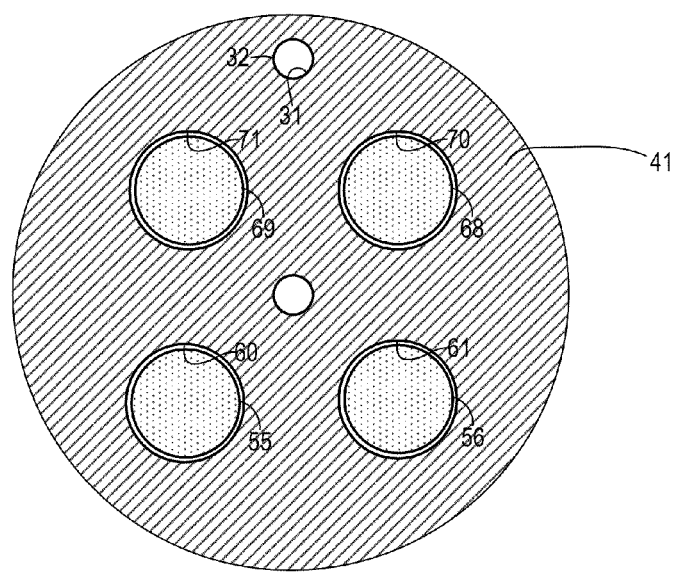

As seen in FIGS. 7 through 9, end cap 17 is attached to neck 19 at a joint 44 using glue, radio frequency welding or other appropriate technique. End cap 17 is formed from plastic or other insulating material, but includes a metallic electrode ring 18 attached (e.g., with glue or other adhesive) to non-conducting portions of end cap 17. The distal end of neck 19 adjacent to joint 44 includes an end wall 46 having multiple holes formed therein. Guide wire tube 32 passes through hole 52, and wires 38 and 39 pass through hole 51. Walls of holes 47 and 48 act as rotational bearings for spindles 55 and 56, respectively. The relative locations of holes in end wall 46 are also discussed below in connection with FIG. 13. A plurality of holes are also formed in distal outer face 41 of end cap 17. An outer lip of guide wire tube 32 is sealed to the edges of hole 31. Spindles 55 and 56 pass through holes 60 and 61, with the walls of holes 60 and 61 also acting as rotational bearings for spindles 55 and 56. The relative locations of holes in end cap 17 are discussed below in connection with FIG. 14.

A first gear 62 is fixedly attached to spindle 55 on the proximal side of end wall 46. To avoid confusing the drawings with unnecessary detail, gears are represented as smooth disks with gear teeth omitted. Head 11 is fixedly attached to the opposite end of spindle 55 at distal outer face 41 of end cap 17. In a similar manner, head 14 is fixedly attached to one end of spindle 56 and a gear 63 is fixedly attached to the other end of spindle 56. A second gear 72 is fixedly attached to spindle 56 on the distal side of end wall 46.

Heads 11 and 14 and spindles 55 and 56 are formed from metal and are conductive. Drive shaft 36 is attached to gear 62. The portion of drive shaft 36 attached to gear 62 is formed from a non-conductive polymer so as to insulate drive motor 35 from spindle 55. In some embodiments, the non-conductive portion of shaft 36 is attached to a metal portion of shaft 36 by a separate coupler not shown in the drawings. Two branches 38a and 38b from wire 38 are connected to conductive brushes 65 and 66. Return wire 39 is attached to electrode ring 18.

As seen in FIG. 8, head 13 is fixedly attached to an end of spindle 68 at the distal outer face 41 of end cap 17. Spindle 68 passes through hole 70 in end cap 17 and hole 49 in end wall 46, with the walls of holes 70 and 49 forming rotational bearings for spindle 68. Similarly, head 12 is fixedly attached to spindle 69, with spindle 69 passing through holes 71 and 50, and with the walls of holes 71 and 50 forming rotational bearings for spindle 69. Gears 73 and 74 are fixedly attached to spindles 68 and 69, respectively, on the distal side of end wall 46. Heads 13 and 12 and spindles 68 and 69 are formed from metal and are conductive. Two branches 38d and 38c from wire 38 are connected to conductive brushes 77 and 78.

Figure 10:
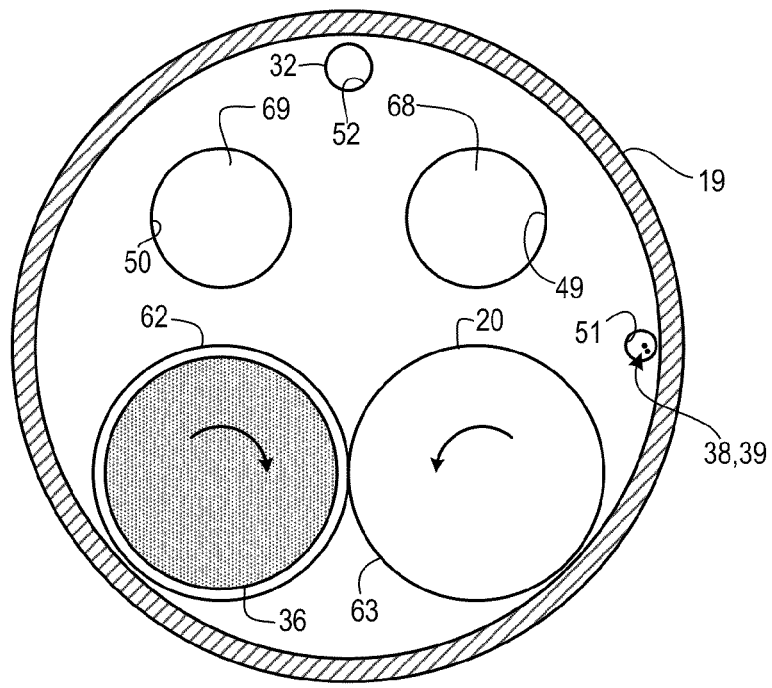
FIGS. 10 through 14 are axial cross-sectional views of the distal end of the instrument of FIG. 1 taken from the locations shown in FIGS. 7 and 8.

FIGS. 10 through 14 are axial cross-sectional views of the distal end of instrument 10 taken from the locations shown in FIGS. 7 and 8. Although each of FIGS. 7 and 8 is a longitudinal cross-sectional view only showing a half of the distal end, each of the views in FIGS. 10-14 is of the entire axial cross section from the locations indicated in FIGS. 7 and 8. For example, FIG. 10 is an axial cross-sectional view showing the half of instrument 10 above the cut line formed by arrows 10 in FIG. 7 "rejoined" to the half of instrument 10 that is located above the cut line formed by arrows 10 in FIG. 8.

Figure 11:
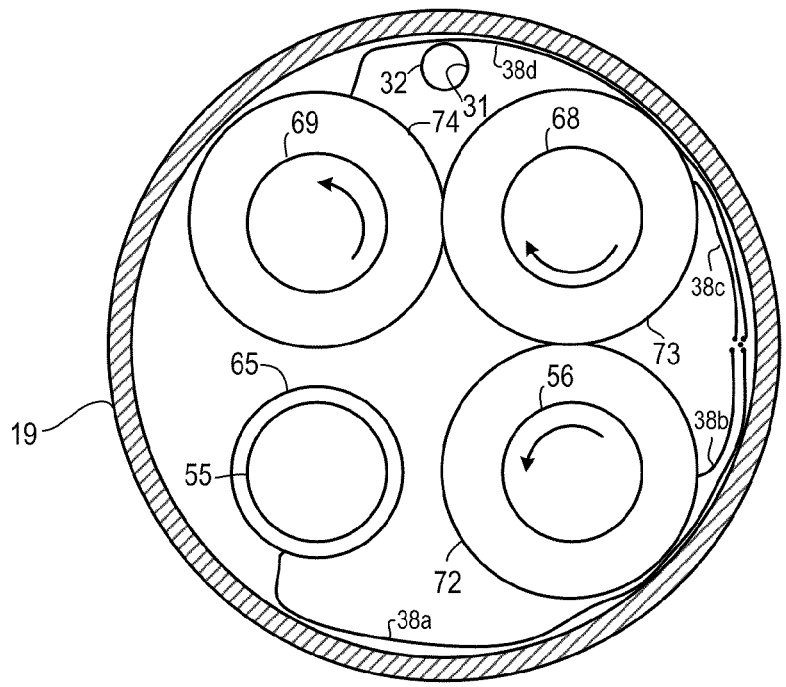
Figure 12:
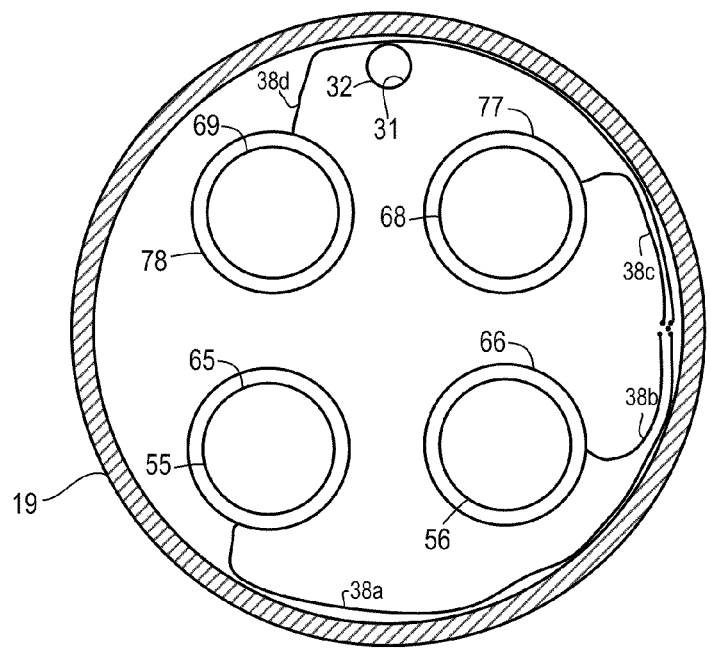

As can be seen in FIG. 10, rotation of gear 62 causes rotation of gear 63. Because gear 63 and gear 72 are attached to spindle 56, gear 72 thus rotates when gear 63 rotates. Accordingly, and as seen in FIG. 11, rotation of gear 72 causes rotation of gear 73, which in turn causes rotation of gear 74. As can thus be appreciated, rotational torque applied to drive shaft 36 rotates all four spindles 55, 56, 68 and 69, and thus all four heads 11, 14, 13 and 12. In at least some embodiments, gears 62, 63, 72, 73 and/or 74 are formed from a hard rubber-like compound so as to increase static friction between gears. In some such embodiments, gears 62, 63, 72, 73 and/or 74 do not have actual teeth, and instead rely on static friction between contacting gear surfaces to transfer rotational torque.

As the heads rotate when instrument 10 is in operation, teeth 15 on the outer head surfaces mechanically cut away tissue as a physician pushes the distal end of instrument 11 into contact with that tissue. Simultaneously, electrical energy is supplied to the outer surfaces of the heads via power supply wire 38, branches 38a through 38d and brushes 65, 66, 77 and 78 (see FIG. 12), and the metal of spindles 55, 56, 68 and 69. As the teeth 15 on the rotating heads mechanically remove one or more layers of tissue, electrical energy applied to the outer surfaces of the heads cauterizes blood vessels, etc. in underlying tissue layers that are exposed by tissue removal. In at least some embodiments, instrument 10 can be configured to operate in either a monopolar or a bipolar cauterization mode. In monopolar mode, high frequency RF energy is conveyed by wire 38; electrode 18 and wire 39 are not used. In bipolar mode, electric current is supplied by wire 38 to heads 11 through 14; return current is received by from electrode 18 by wire 39.

Figure 15:
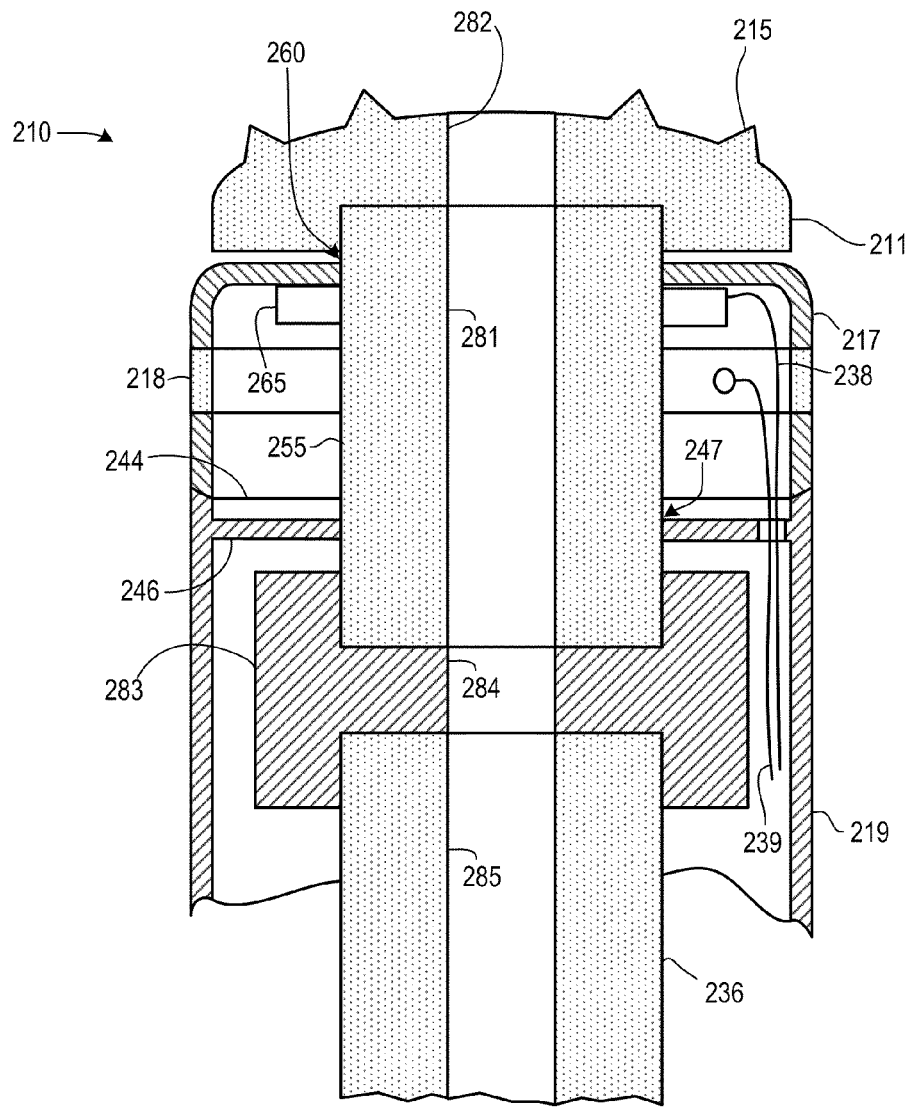
FIG. 15 is a longitudinal cross-sectional view of a distal end of a combination tissue removal and electrical cauterization surgical instrument according to some additional embodiments.
Figure 16:
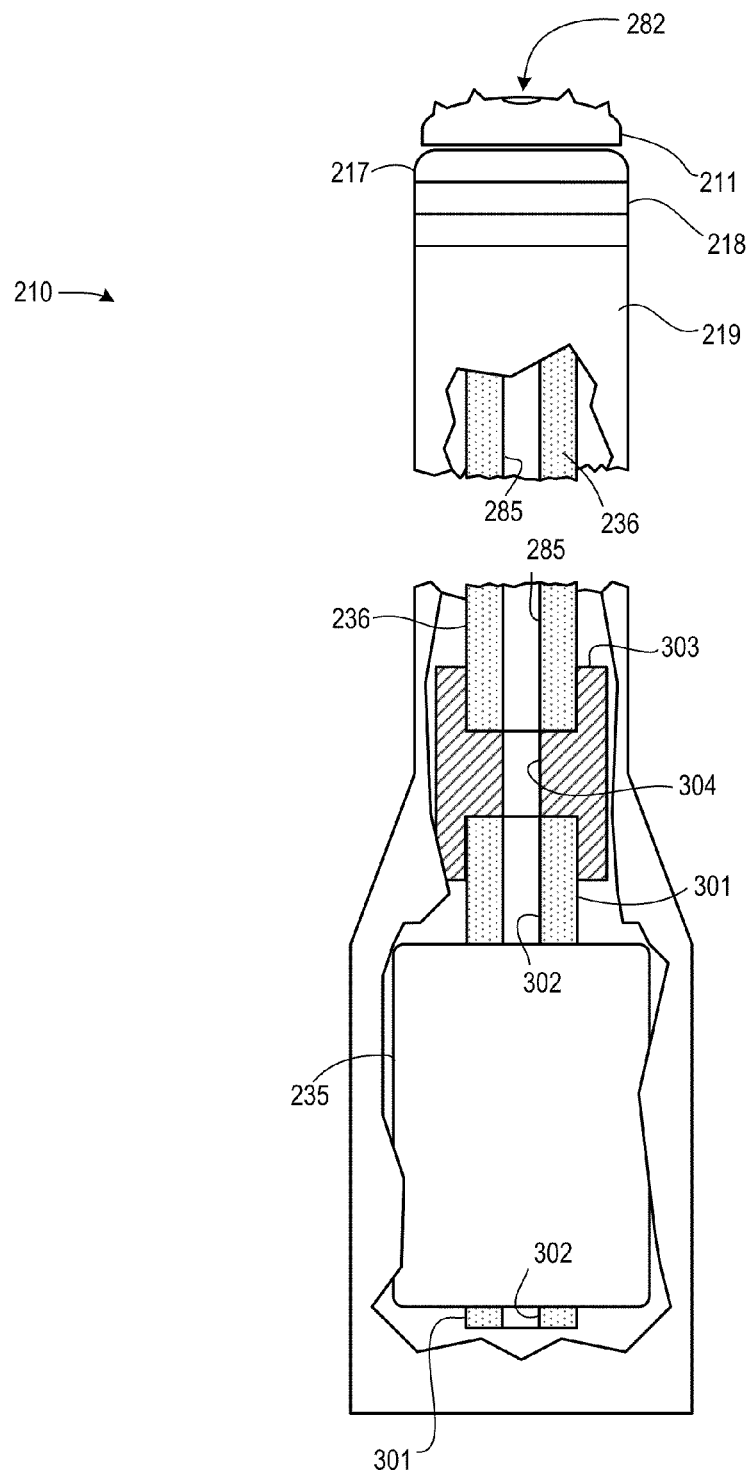
FIG. 16 is a partial cutaway view of the instrument of FIG. 15.

In other embodiments, a combination tissue removal and cauterization instrument may include fewer rotating heads. For example, one head can be omitted so as to provide room for a larger diameter tube to deliver and/or remove larger volumes of liquid from an operative region. In still other embodiments, only a single larger-diameter rotating head is present, with that head being located in the center of the distal end. FIG. 15 is a longitudinal cross-sectional view of a distal end of a surgical instrument 210 according to one such embodiment. In the embodiment of FIG. 15, a single metal drive spindle 255 passes through a hole 247 in an end wall 246 of a neck section 219 and through a hole 260 in an end cap 217. End cap 217 is sealed to neck 219 at a joint 244. A single metal head 211 is fixedly attached to spindle 255 and has a plurality of teeth 215 on its outer surface. A central bore 281 in spindle 255 is generally aligned with a hole 282 in head 211. A drive shaft 236 is coupled to spindle 255 with a nonconductive coupler 283 so as to insulate a drive motor 235 (FIG. 16) from head 211. Coupler 283 and drive shaft 236 also have hollow bores 284 and 285, respectively. As seen in FIG. 16, a partial cutaway view of instrument 210 with a portion of neck 219 and shaft 236 also removed, drive shaft 236 is coupled to an output shaft 301 of motor 235 by a coupler 303 having a bore 304. Drive shaft 301 of motor 235 is a hollow thru-shaft that extends the length of motor 235 and provides an entrance to the thru-shaft bore 302 (and thus to the bore of shaft 236, coupler 283, spindle 255 and head 211) at the proximal face of drive motor 235. Shaft 236, coupler 303 and shaft 301 are shown in cross section in FIG. 16 so as to illustrate the bores thereof. In the embodiment of FIG. 15, the rotational axis of drive motor 235 is concentric with the rotational axis of head 211, and a guide wire conduit is provided through hole 282 and bores 281, 284, 285, 304 and 302. Similar to the embodiments of FIGS. 1-14, electrical cauterization energy can be supplied to the outer surface of head 211 via brush 265 and wire 238 (and returned by electrode 218 and wire 239 in bipolar mode).

Figure 17:
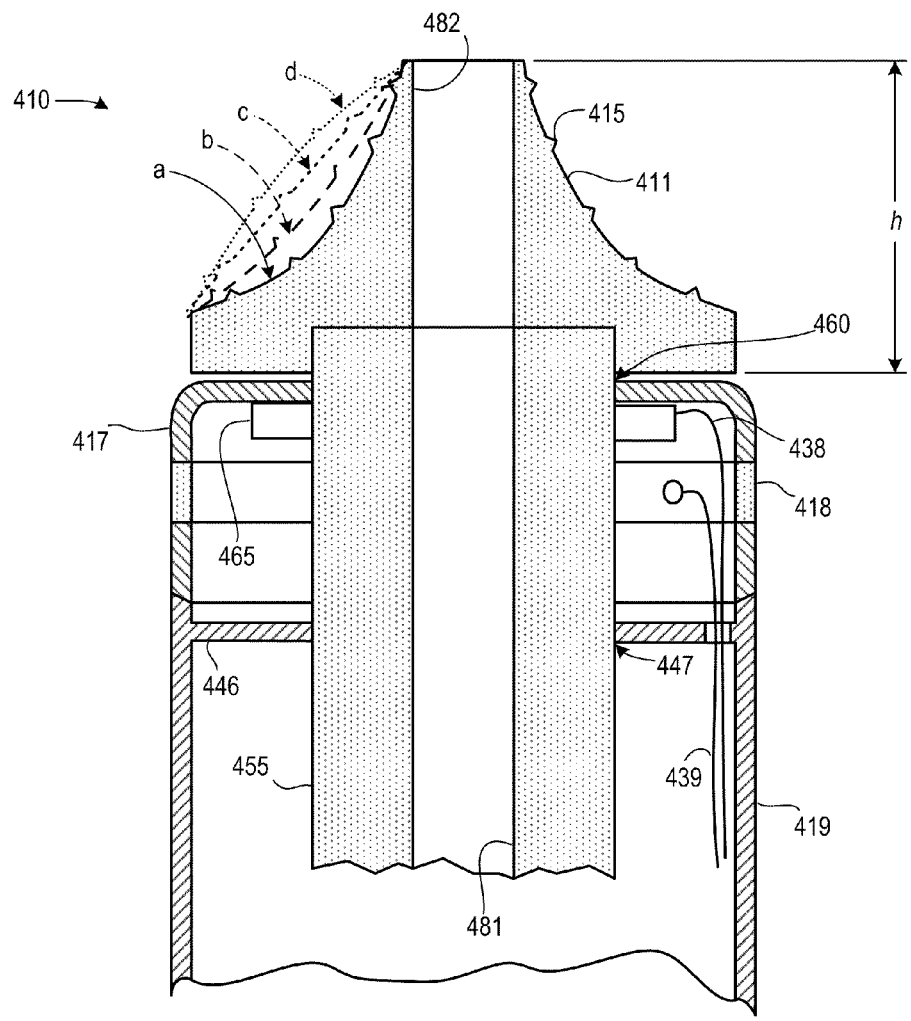
FIGS. 17 through 19 are longitudinal cross-sectional views of combination tissue removal and electrical cauterization surgical instrument according to various additional embodiments.

In yet other embodiments, rotating heads have different contours and/or different types of surface protrusions adapted to remove specific types of tissue. For example, FIG. 17 is a longitudinal cross-sectional view of a combination tissue removal and electrical cauterization surgical instrument 410 according to one such embodiment. As shown in FIG. 17, instrument 410 has a single head 411. Instrument 410 is generally similar to instrument 210 of FIGS. 15-16, except that head 411 has an outer contour designed to fit closely into a spinal facet joint during a spinal facet debridement procedure. For some embodiments intended for use in spinal facet procedures, height h of head 411 may be approximately 3 to 5 mm. For at least some embodiments designed for lumbar facet joints, the sides of head 411 may have a curved profile a. For certain embodiments designed for cervical and thoracic facet joints, profiles with less curvature (profile b) or with generally flat profiles (c) may be desired. In some embodiments, an outwardly curving profile d may be desired. In at least some embodiments designed for facet joint debridement and denuding, teeth 411 (and/or teeth described herein in connection with other drawing figures) are configured to denude tissues from the bone without digging into the bone.

For example, the teeth may be more angulated (so as to strip bone) and not front-cutting or boring in nature. Other elements of the embodiment of FIG. 17 that are similar to the elements in the embodiment of FIGS. 15 and 16 have been given similar reference numbers, but with 200 added. For example, neck 419 of FIG. 17 is generally similar to neck 219 of FIG. 15.

Figure 18:
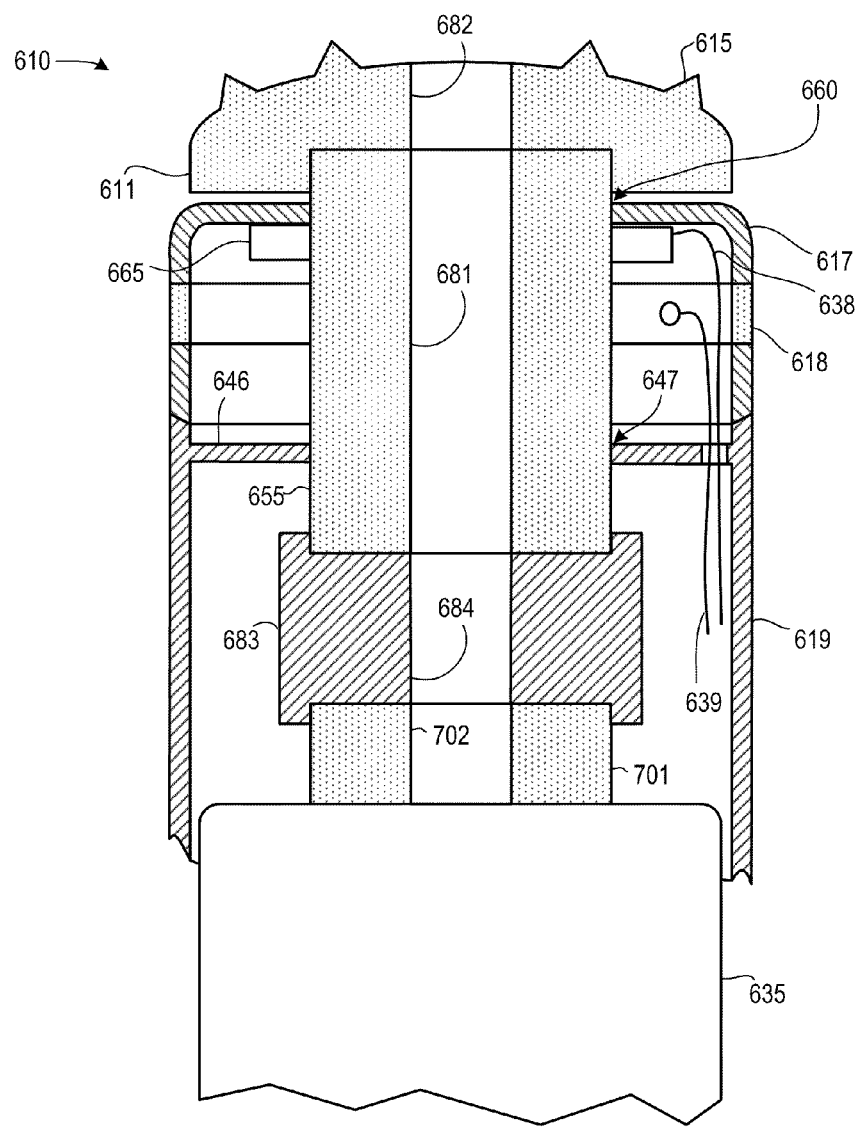

FIG. 18 is a longitudinal cross-sectional view of a combination tissue removal and electrical cauterization surgical instrument 610 according to certain additional embodiments. Instrument 610 is generally similar to instrument 210 of FIGS. 15 and 16, except that drive motor 635 is located in the distal end of neck 619. For simplicity, motor 635 is not shown in cross section. In the embodiment of FIG. 18, the output shaft 701 of drive motor 635 is directly coupled (via nonconductive coupler 683 having bore 684) to metal spindle 655 (having bore 681), with spindle 655 attached to metal head 611 (having hole 682). A separate tube (not shown) connects the opening of bore 702 of the drive motor 635 thru-shaft 701 on the opposite side of motor 635 to a guide wire exit hole on a proximal face of instrument 610. Other elements of the embodiment of FIG. 18 that are similar to the elements in the embodiment of FIGS. 15 and 16 have been given similar reference numbers, but with 400 added.

Other embodiments may also employ different types of couplings and other mechanisms to transfer mechanical energy from a motor or other movement power source to one or more rotating heads. For example, a single centrally-located drive shaft may have a bevel gear formed on its end. That bevel gear would then act on corresponding bevel gears formed on the ends of spindles attached to the rotating heads. In still other embodiments, a guide wire tube is attached to the outside of the instrument so as to provide more space inside the instrument for other components.

Figure 19:
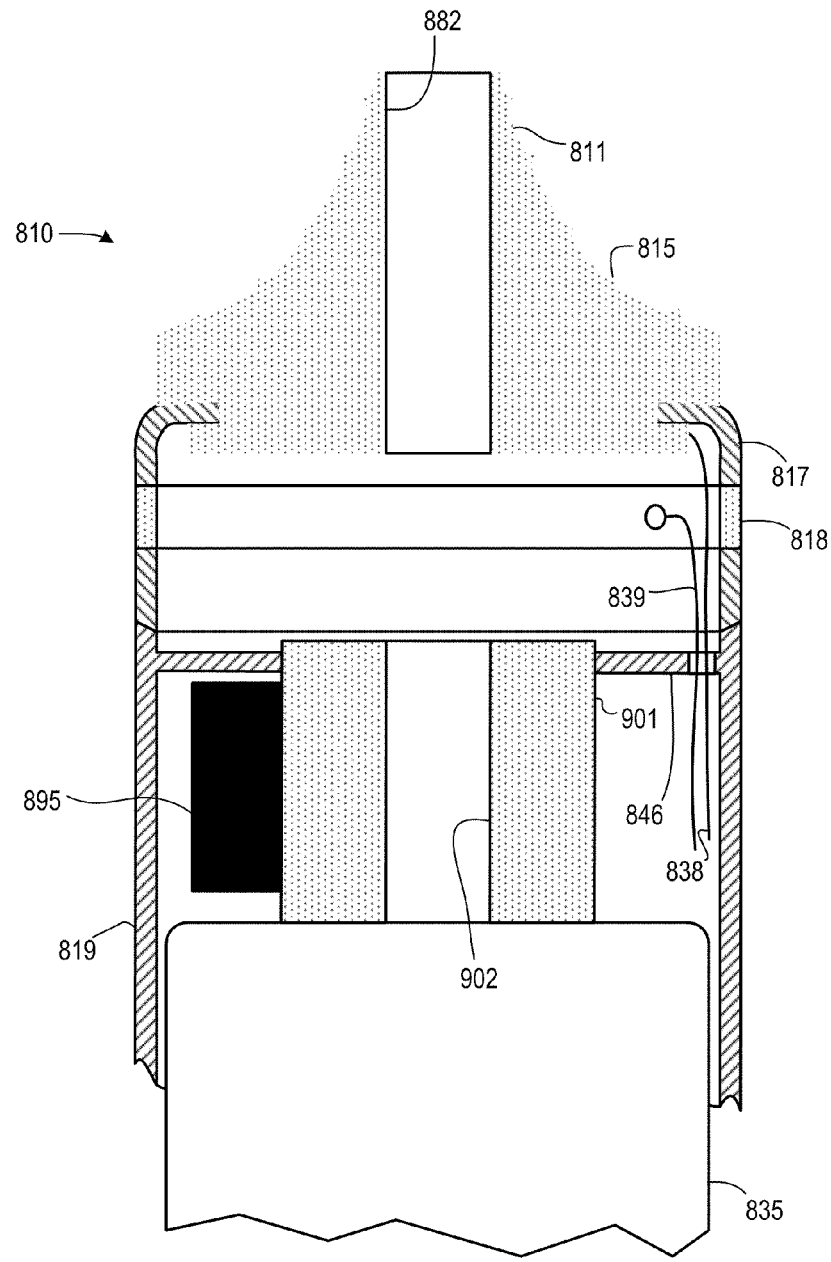

In still other embodiments, tissue removal/cauterizing heads are not rotated relative to the instrument, but are instead moved in a vibratory manner. FIG. 19 is a longitudinal cross-sectional view of a combination tissue removal and electrical cauterization surgical instrument 810 according to certain of those vibratory embodiments. In the embodiment of FIG. 19, a drive motor 835 is located near the distal end of instrument 810. For simplicity, motor 835 is not shown in cross section. The output shaft 901 of drive motor 835 is rotatably supported by end wall 846 of neck 819, but is not rotatably coupled to head 811. Instead, metal head 811 is fixedly attached to nonconductive end cap 817. An eccentric weight 895 is attached to the drive shaft 701 of motor 836. In operation, rotation of drive shaft 701 induces vibrations in the distal end of instrument 810. Those vibrations cause a mechanical cutting action by teeth 815 against tissue into which head 811 is placed in contact. A wire 838 supplies electrical cauterization energy to head 811. A return wire (for bipolar mode operation) is attached to electrode 818. A guide wire passage is formed by a bore 882 in head 811, by a bore 902 in the thru-shaft 901 drive motor 835, and by a separate tube (not shown) connecting the opening of bore 902 on the opposite side of motor 835 to a guide wire exit hole on a proximal face of instrument 810.

Figure 20:
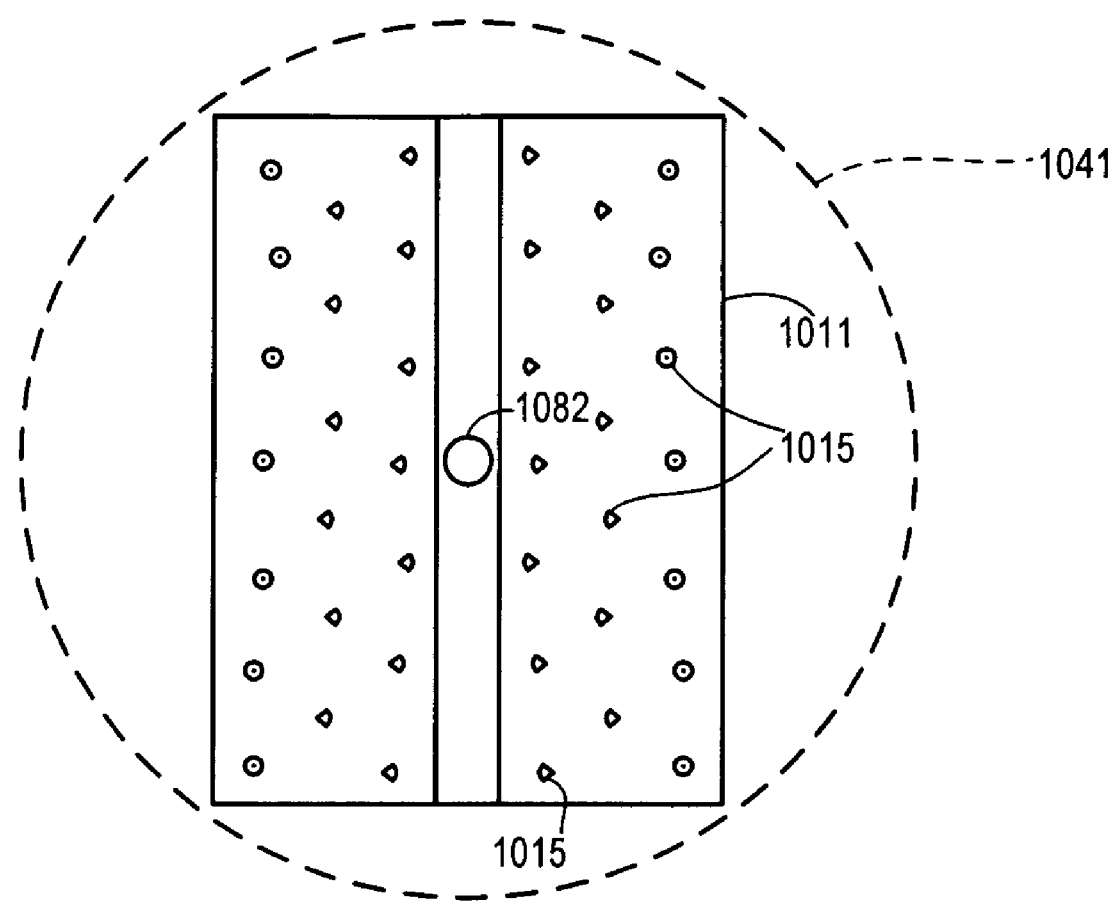
FIG. 20 is an end view of a non-circular cutting and cauterizing head.

Although the cutting/cauterizing heads in various previously-described embodiments have a round cross-section, this need not be the case. For example, a vibratory embodiment such as instrument 810 (FIG. 19) could have a chisel-shaped head. In one such embodiment, a side longitudinal cross-section of the head would be similar to the head cross-section shown in FIG. 19, but the head would be rectangular in shape when viewed on end. An end view of such a head 1011 having teeth 1015 and a guide wire hole 1082 is seen in FIG. 20. An outline of a distal outer surface 1041 is also shown, In at least some embodiments, a combination tissue removal and cauterization instrument is designed as a disposable, single-use item. In some such embodiments, this would permit use of lighter weight and smaller components because the instrument need not be able to withstand sterilization in an autoclave. In still other embodiments, an instrument is configured so that cutting heads may be removed and replaced with new heads, with the removed heads being disposable.

In certain embodiments, rotational torque or vibratory motion is supplied by a source other than an electric motor, or is supplied by an electric motor that is contained in a separate component. For example, a combination tissue removal and cauterization instrument similar to one or more of the above embodiments could be configured as an attachment to a separate hand piece housing a motor or other drive source. As another example, compressed air could be used to drive a micro turbine within an instrument.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and their practical application to enable one skilled in the art to utilize the present invention in various embodiments and with various modifications as are suited to the particular use contemplated. The features of the embodiments described herein may be combined in all possible combinations of methods and apparatuses.

The invention claimed is:

1. An apparatus comprising:
a main body having an elongated neck and a distal end sized for insertion through a cannula so as to place the distal end in a surgical site within a body of a patient;
a first head coupled to the main body at the distal end, wherein
the first head is rotatable relative to the main body,
the first head includes an outer surface configured to remove tissue by mechanical cutting action, and
at least a portion of the first head outer surface is electroconductive;
a rotating member configured to couple the first head to a source of rotational torque; and
at least one conductor providing a path for transfer of electrical cauterization energy to the electroconductive portion of the first head outer surface.

2. The apparatus of claim 1, further comprising an input connector located on the main body and configured for attachment to a source of electrical cauterizing energy, and wherein the at least one conductor transfers electrical cauterization energy from the input connector to the electroconductive portion of the first head outer surface.

3. The apparatus of claim 1, further comprising second, third and fourth heads also coupled to the main body at the distal end, wherein
each of the second, third and fourth heads is rotatable relative to the main body,
each of the second, third and fourth heads includes an outer surface configured to remove tissue by mechanical cutting action, at least a portion of the outer surfaces of each of the second, third and fourth heads is electroconductive, application of rotation torque to the rotating member causes rotation of the first, second, third and fourth heads, and the at least one conductor provides a path for transfer of electrical cauterization energy to the electroconductive portions of the second, third and fourth head outer surfaces.

4. The apparatus of claim 1, further comprising a first guide wire hole formed in a distal end face of the distal end and a second guide wire hole located on an external portion of the apparatus displaced proximally from the first guide wire hole, and wherein the apparatus is configured to permit internal passage of a guide wire between the first and second guide wire holes.

5. The apparatus of claim 1, wherein the distal end sized for insertion through a cannula has a dimension perpendicular to a longitudinal axis of between 5 and 15 mm.

6. The apparatus of claim 1, wherein a longitudinal length of a portion of the apparatus configured for insertion through a cannula is between 6 and 20 mm.

7. The apparatus of claim 1, wherein the first head is the only head on the apparatus.

8. The apparatus of claim 1, wherein the first head has a cross section adapted to conform to a human spinal facet joint.

9. The apparatus of claim 1, wherein the apparatus is configured for alternately performing electrical cauterization in monopolar mode or in bipolar mode.

10. The apparatus of claim 1, further comprising a drive motor located within the main body and having an output shaft coupled to the rotating member.

11. The apparatus of claim 1, wherein the outer surface comprises a plurality of teeth extending from a convex curve.

12. An apparatus, comprising:
a main body having an elongated neck and a distal end sized for insertion through a cannula so as to place the distal end in a surgical site within a body of a patient;
a head coupled to the main body at the distal end, wherein the head includes an outer surface configured to remove tissue by mechanical cutting action, and
at least a portion of the head outer surface is electroconductive;
a means for inducing movement of the head so as to effect the mechanical cutting action; and
at least one conductor providing a path for transfer of electrical cauterization energy to the electroconductive portion of the head outer surface.

13. The apparatus of claim 12, wherein the means is configured to induce rotational movement to the cutting head.

14. The apparatus of claim 12, wherein the means is configured to induce vibrational movement to the cutting head.

15. The apparatus of claim 12, wherein the outer surface comprises a plurality of teeth extending from a convex curve.

* * * * *